United States Patent
Sirdesai

(10) Patent No.: US 9,044,405 B2
(45) Date of Patent: Jun. 2, 2015

(54) COMPOSITION HAVING A REDUCED EXOTHERM IN ACTINIC CURING OF URETHANE (METH)ACRYLATE OLIGOMERS ON FINGERNAILS

(71) Applicant: O P I Products, Inc., North Hollywood, CA (US)

(72) Inventor: Sunil J. Sirdesai, Irvine, CA (US)

(73) Assignee: O P I Products, Inc., North Hollywood, CA (US)

(*) Notice: Subject to any disclaimer, the term of this patent is extended or adjusted under 35 U.S.C. 154(b) by 79 days.

(21) Appl. No.: 13/778,765

(22) Filed: Feb. 27, 2013

(65) Prior Publication Data

US 2014/0242011 A1   Aug. 28, 2014

(51) Int. Cl.

| | |
|---|---|
| *A61Q 3/00* | (2006.01) |
| *A61K 8/02* | (2006.01) |
| *A61K 8/37* | (2006.01) |
| *A61Q 3/02* | (2006.01) |
| *A61K 8/87* | (2006.01) |
| *C08K 5/00* | (2006.01) |
| *C09D 175/16* | (2006.01) |
| *A61K 8/35* | (2006.01) |
| *A61K 8/55* | (2006.01) |
| *A61K 8/81* | (2006.01) |

(52) U.S. Cl.
CPC ... *A61K 8/37* (2013.01); *A61Q 3/02* (2013.01); *A61K 8/87* (2013.01); *C08K 5/005* (2013.01); *C09D 175/16* (2013.01); *A61K 8/35* (2013.01); *A61K 8/55* (2013.01); *A61K 8/8152* (2013.01); *A61K 2800/24* (2013.01); *A61K 2800/81* (2013.01)

(58) Field of Classification Search
None
See application file for complete search history.

(56) References Cited

U.S. PATENT DOCUMENTS

| | | |
|---|---|---|
| 6,423,381 B1 | 7/2002 | Colton et al. |
| 2002/0115756 A1 | 8/2002 | Lin et al. |
| 2005/0203202 A1 | 9/2005 | Weine |
| 2007/0214989 A1 | 9/2007 | Arnold et al. |
| 2010/0056722 A1 | 3/2010 | Thomas et al. |
| 2011/0120546 A1 | 5/2011 | Nesbitt et al. |
| 2011/0257273 A1 | 10/2011 | Yabuuchi et al. |
| 2012/0276028 A1 | 11/2012 | Kojima et al. |
| 2013/0263875 A1 * | 10/2013 | Burgess et al. ............ 132/200 |

FOREIGN PATENT DOCUMENTS

| | | |
|---|---|---|
| CN | 102766399 | 11/2012 |
| EP | 1508327 A1 * | 2/2005 |

OTHER PUBLICATIONS

PCT Search Report and Written Opinion mailed May 9, 2014, PCT Appln. No. PCT/US2014/018227, 11 pages.
BASF, "Coatings that stay looking good: BASF performance additives", Retrieved from the Internet at basf.com (retrieved on Apr. 28, 2014), (Aug. 2, 2011), 32 pages.
BASF, "UV Filters", Retrieved from the Internet at basf.com (retrieved on Apr. 28, 2014), (Nov. 2011), 18 pages.
CIBA Specialty Chemicals, "Photoinitiators for UV Curing: Key Products Selection Guide", Retrieved from the Internet at forums.reprap.org (retrieved on Apr. 28, 2014), (Oct. 2003), 8 pages.

* cited by examiner

*Primary Examiner* — Susan Tran
(74) *Attorney, Agent, or Firm* — Blakely Sokoloff Taylor & Zafman LLP

(57) ABSTRACT

A nail coating composition having a reduced exotherm during actinic curing of the coating on a nail. The composition may include a curable resin, a monomer, a photoinitiator, a chemical filter capable of absorbing ultraviolet (UV) light and reducing exotherm, and an additive.

22 Claims, No Drawings

COMPOSITION HAVING A REDUCED EXOTHERM IN ACTINIC CURING OF URETHANE (METH)ACRYLATE OLIGOMERS ON FINGERNAILS

BACKGROUND

1. Field

An embodiment of the invention is directed to a composition and method for reducing exotherm in actinic curing of urethane (meth)acrylate oligomers on fingernails. Other embodiments are also described and claimed.

2. Background

Urethane meth(acrylate) oligomer based nail formulations are used in the nail care industry to form durable coatings on fingernails. Such formulations also include monomers which form polymer chains within the formulation upon curing. The formation of polymer chains, however, is an exothermic reaction which generates heat. The heat that is generated has to be dissipated quickly, so that the client does not face any discomfort. Adding additives like pigments and glitters sometimes increases the polymerization rate tremendously such that the system does not have time to dissipate the heat quickly, causing the client extreme discomfort due to heat.

One way to mitigate this undesired phenomenon is to adjust the amount of photoinitiator(s) (PI) in the starting base. It would, however, be extremely difficult from an inventory standpoint to maintain so many different bases. In addition, since additives (e.g., pigments and glitters) vary from batch to batch, PI(s) would still have to be adjusted in the base designated for that particular SKU. Though feasible, this would be less than an ideal solution to the problem.

Another possible solution is to keep the same base formation but change the intensity of irradiated light. This is not a practical solution for lamps that will be used in salons. Even if lamps exhibiting different intensities were feasible, the manicurist has to know beforehand the level of intensity that a particular batch of gel needs to cure to form a coat on a fingernail without creating a heat spike. The package would therefore have to carry information regarding the intensity to be used for that particular batch, another hurdle to making a successful brand.

SUMMARY

An embodiment of the invention is directed to a nail care composition which includes a chemical filter (ultraviolet (UV) absorber) that can reduce an intensity of heat spikes during curing of the composition on the user's nail. As previously discussed, heat spikes, also known as exotherm, are a phenomenon that occurs during the polymerization process and, in some cases, can be enhanced by the presence of additives (e.g., pigments or glitter) and other ingredients within the composition. In this aspect, the chemical filter is designed to absorb the UV light of the frequency at which it is excited by the actinic radiation. The composition may further include photoinitiators (PIs) which are dissociated in one or more wavelength regions. The chemical filter can be such that it absorbs light in one of the wavelength regions within which the PIs can be dissociated, but does not absorb light within other wavelength regions. It was unexpectedly found that using the complementary PIs and filtering light in one region, depending on light source, not only reduces exotherm but allows polymerization to proceed smoothly and provide a long-lasting durable coating. Suitable chemical filters may include, but are not limited to, 2-ethylhexyl-3-(4-methoxyphenyl)-2-propenoate also known as PARSOL® MCX, 3-(4-methyl)benzylidene-bornan-2-one also known as PARSOL® 5000, 1-(4-tertbutylphenyl)-3-(4-methoxyphenyl)-propane-1, 3 dione also known as PARSOL® 1789, 2-cyano-3,3-diphenyl acrylic 2-ethyl-hexyl ester also known as PARSOL® 340 and 2,2'-(2,5-thiophenediyl)bis(5-tert-butylbenzoxazole) also known as UVITEX® OB.

The above summary does not include an exhaustive list of all aspects of the embodiments disclosed herein. It is contemplated that the embodiments may include all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

In this section we shall explain several preferred embodiments of the invention. Whenever the ingredients, ranges and other aspects of the formulations described in the embodiments are not clearly defined, the scope of the embodiments is not limited only to the formulations shown, which are meant merely for the purpose of illustration. Also, while numerous details are set forth, it is understood that some embodiments may be practiced without these details. In other instances, well-known structures and techniques have not been shown in detail so as not to obscure the understanding of this description.

The instant invention is directed to a composition designed to provide overlays (e.g., a nail coating) on the nail of a user. In one embodiment, the composition may be a composition which, when applied to the nail, forms a gel coating over the nail. The composition may be a photoreactive composition in that it cures (i.e., forms a gel coating) when exposed to a light source. In order to reduce a heat spike, also referred to as exotherm, which may occur during curing of the composition on the user's nail, the composition may include a chemical filter which absorbs UV light in the frequency range of the actinic radiation (e.g., a frequency range of the light source). In some embodiments, the chemical filter is capable of reducing exotherm by at least 90 percent, for example, by at least 95%, for example, from about 95% to about 98%, as compared to a nail coating composition without the chemical filter. As a result of the exotherm reduction, the heat level felt by a user during curing of the composition on the nail is significantly reduced to a level where it is not uncomfortable to the user, and in some cases barely noticeable.

In some embodiments, the chemical filter is capable of absorbing light within an ultraviolet A (UVA) or ultraviolet B (UVB) frequency range. For example, the chemical filter may absorb light within a frequency range of from about 100 nm to about 405 nm, or from 280 nm to 315 nm, or from 315 nm to 405 nm. It is further contemplated that two or more chemical filters capable of absorbing light within different frequency ranges may be included in the composition. For example, a chemical filter which absorbs light within a UVA frequency range and a chemical filter which absorbs light within a UVB frequency range may be included in the composition.

Representative chemical filters may include, but are not limited to, 2-ethylhexyl-3-(4-methoxyphenyl)-2-propenoate also known as PARSOL® MCX, 3-(4-methyl)benzylidene-bornan-2-one also known as PARSOL® 5000, 1-(4-tertbutylphenyl)-3-(4-methoxyphenyl)-propane-1,3 dione also known as PARSOL® 1789, 2-cyano-3,3-diphenyl acrylic 2-ethyl-hexyl ester also known as PARSOL® 340 and 2,2'-(2,5-thiophenediyl)bis(5-tert-butylbenzoxazole) also known as UVITEX® OB. In one embodiment, the composition may include the chemical filter in any amount sufficient to reduce an exotherm or heat spike which may occur during curing of the composition on the user's nail. For example, the chemical filter may be provided in an amount of from about 1 percent to about 15 percent, or from about 3 percent to about 10 percent, for example, or from 5 percent to 7 percent by weight of the total composition.

It is further contemplated that in some embodiments, the chemical filter may be selected to filter (i.e., absorb light) within a frequency range that can be used to excite a photoinitiator(s) included in the composition. For example, in some embodiments, the composition includes a photoinitiator which is excitable within a UVA radiation range. In this aspect, the chemical filter is one which absorbs light within a UVA radiation range which is emitted from a light source. In other embodiments, the composition includes a photoinitiator which is excitable within a UVB radiation range. In this aspect, the chemical filter absorbs light within the UVB radiation range, which is emitted from the light source. It was unexpectedly found that using complimentary PI(s) and chemical filters which filter light in one region depending on the light source (e.g., UVA or UVB) not only reduces exotherm (for example, by at least 90 percent) but allows for polymerization to proceed smoothly and provide a long-lasting durable coating on the user's nail. In particular, PIs are excited most efficiently by light within a certain wavelength or wavelength range. They can also, however, be excited less efficiently by light within wavelengths outside of this region. This inefficient excitation contributes to the exotherm of the polymerization. Since the chemical filter is selected such that it only allows light within a range which excites the PI to react with the PI, while blocking out light within other, less efficient, wavelength ranges, exotherm can be reduced.

Representative photoinitiators may include any photoinitiators excitable within a visible light or UV radiation range, more specifically, a UVA or UVB radiation range. For example, suitable photoinitiators may include, but are not limited to, one or more of benzoyl isopropanol, trimethylbenzoyl diphosphine oxide, trimethylbenzoyl diphenylphosphine oxide, hydroxycyclohexyl phenyl ketone, and ethyl trimethylbenzoylphenylphosphinate. The composition may include the photoinitiator in any amount sufficient to facilitate formation of a gel overlay on a user's nail. For example, in one embodiment, the composition may include the photoinitiator in an amount of from about 1 percent to about 10 percent, for example, from about 4 percent to about 6 percent, or from about 5 percent to about 5.5 percent by weight of the total composition.

In addition to a chemical filter and photoinitiator, the composition may include a curable resin(s), a monomer(s), a thixotrope(s), a solvent(s), a plasticizer(s), a suspending agent(s), a pigment(s) and/or a colorant(s). The curable resin may be, but is not limited to, urethane acrylate/methacrylate oligomers, for example, urethane (meth)acrylate. In one embodiment, the composition may include the curable resin in any amount sufficient to form a coating on a user's nail. For example, in one embodiment, the composition may include the curable resin in an amount of from about 30 percent to about 65 percent, for example, from about 40 percent to about 55 percent, or from 49 percent to 52 percent by weight of the total composition.

The monomer may be any type of monomer suitable for use within a composition for forming a nail coating. In some cases, the monomer may also serve as a crosslinker within the composition. For example, in one embodiment, the monomer may be, but is not limited to, one or more of triethylene glycol dimethacrylate, hydroxypropyl methacrylate, isobornyl methacrylate, isobornyl acrylate, hydroxyethyl methacrylate (HEMA), hema maleate, PEG-4 dimethacrylate and ethyl methacrylate. The composition may include the monomer in any amount sufficient to facilitate formation of a coating on a user's nail. For example, in one embodiment, the composition may include the monomer in an amount of from about 20 percent to about 55 percent, for example, from about 30 percent to about 45 percent, or from 35 percent to 40 percent by weight of the total composition.

A suitable thixotrope may include, but is not limited to, polyquaternium 37. The thixotrope may be provided in any amount sufficient to facilitate formation of a coating on a user's nail, for example, from about 2 percent to about 10 percent, or from about 4 percent to 6 percent, or at least 5 percent by weight of the total composition.

A suitable solvent may include, but is not limited to, propylene glycol dicaprylate. The solvent may be provided in any amount sufficient to facilitate formation of a coating on a user's nail, for example, from about 0.5 percent to about 10 percent, or from about 1 percent to 5 percent, or at least 2 percent by weight of the total composition.

A suitable plasticizer may include, but is not limited to, PPG-1 trideceth 6 or dimethicone. The plasticizer may be provided in any amount sufficient to facilitate formation of a coating on a user's nail, for example, from about 0.5 percent to about 10 percent, or from about 1 percent to 5 percent, or at least 2 percent by weight of the total composition.

The suspending agent may be used to suspend an additive such as a pigment or glitter within the composition. In one embodiment, the suspending agent is fumed silica. The fumed silica may form bonds with the additive, e.g. glitter, thereby forming particles having a relatively large surface area, which can be suspended within the composition. The fumed silica may be provided in any amount sufficient to suspend an additive, for example, from about 0.1 percent to about 10 percent, or from about 3 percent to 7 percent, or at least 5 percent by weight of the total composition.

An additive(s), pigment(s) and colorant(s) may further be included within the composition to enhance the appearance of the composition when applied to the nail and/or provide the desired aesthetic properties. A representative additive may include, but is not limited to, a glitter. The additive may be provided in any amount sufficient to enhance the appearance of the nail coating, for example, in an amount of from about 0.5 percent to about 10 percent, or from about 2.5 percent to about 5 percent, for example, or from 3 percent to 4 percent by weight of the total composition.

Suitable pigment(s) may include, but are not limited to, titanium dioxide, iron oxide or red 21, in any amount sufficient to achieve a coating of the desired appearance. For example, the composition may include a pigment(s) in an amount of from about 0.5 percent to about 5 percent, or from about 1 percent to about 3 percent by weight of the total composition. It is noted that a pigment(s) may be considered a type of additive therefore the use of the term "additive" herein can be broadly understood as referring to a pigment or other type of additive such as a glitter.

Suitable colorant(s) may include, but are not limited to, Violet 2, Red 30 or any other colorant in any amount sufficient to achieve a coating of the desired appearance. For example, the composition may include a colorant(s) in an amount of from about 0.1 percent to about 5 percent, or from about 0.2 percent to about 0.3 percent by weight of the total composition.

Exemplary nail coating composition formulations are provided below.

Example 1

| Chemical Name | Function | Weight Percent (%) |
| --- | --- | --- |
| Urethane Acrylate/Methacrylate Oligomers | Curable Resin | 51.5 |
| Triethylene Glycol Dimethacrylate | Monomer/Crossslinker | 22 |
| Benzoyl Isopropanol | Photoinitiator | 5 |
| Trimethylbenzoyl Diphosphine Oxide | Photoinitiator | 1 |
| Polyquaternium 37 | Thixotrope | 5 |
| Propylene Glycol Dicaprylate | Solvent | 2 |
| PPG-1 Trideceth 6 | Plasticizer | 2 |
| Titanium Dioxide | Pigment | 1 |
| Parsol ® MCX | UVA Filter | 7.5 |
| Glitter | Additive | 3 |

Example 2

| Chemical Name | Function | Weight Percent (%) |
| --- | --- | --- |
| Urethane Acrylate/Methacrylate Oligomers | Curable Resin | 49.5 |
| Hydroxypropyl Methacrylate | Monomer | 11 |
| Isobornyl Methacrylate | Monomer | 8 |
| HEMA | Monomer | 8 |
| Triethylene Glycol Dimethacrylate | Monomer/Crosslinker | 7 |
| Hydroxycyclohexyl Phenyl Ketone | Photoinitiator | 5 |
| Parsol ® MCX | UVA Filter | 7 |
| Ethyl Trimethylbenzoylphenylphosphinate | Photoinitiator | 1 |
| Glitter | Additive | 3.5 |

Example 3

| Chemical Name | Function | Weight Percent (%) |
| --- | --- | --- |
| Urethane Acrylate/Methacrylate Oligomers | Curable Resin | 52.5 |
| Triethyleneglycol Dimethacrylate | Monomer/Crosslinker | 22 |
| Parsol ® MCX | UVA Filter | 10.5 |
| HEMA | Monomer | 7 |
| Hydroxycyclohexyl Phenyl Ketone | Photoinitiator | 3 |
| Benzoyl Isopropanol | Photoinitiator | 2.5 |
| Glitter | Additive | 2.5 |

Example 4

| Chemical Name | Function | Weight Percent (%) |
| --- | --- | --- |
| Urethane Acrylate/Methacrylate Oligomers | Curable Resin | 35 |
| Hydroxypropyl Methacrylate | Monomer | 25 |
| Isobornyl Methacrylate | Monomer | 23 |
| Uvitex ® OB | UVB Filter | 5 |
| Hema Maleate | Monomer | 5 |
| Benzoyl Isopropanol | Photoinitiator | 5 |
| Ethyl Trimethylbenzoylphenylphosphinate | Photoinitiator | 1 |
| Glitter | Additive | 1 |

Example 5

| Chemical Name | Function | Weight Percent (%) |
| --- | --- | --- |
| Urethane Acrylate/Methacrylate Oligomers | Curable Resin | 54.4 |
| PEG-4 Dimethacrylate | Monomer/Crosslinker | 17 |
| Ethyl Methacrylate | Monomer | 10 |
| Hydroxycyclohexyl Phenyl Ketone | Photoinitiator | 5 |
| Trimethylbenzoyl Diphenylphosphine Oxide | Photoinitiator | 1 |
| Parsol ® MCX | UVA Filter | 8.5 |
| Violet 2 | Colorant | 0.1 |
| Glitter | Additive | 4 |

Example 6

| Chemical Name | Function | Weight Percent (%) |
| --- | --- | --- |
| Urethane Acrylate/Methacrylate Oligomers | Curable Resin | 48.2 |
| Triethylene Glycol Dimethacrylate | Monomer/Crosslinker | 24 |
| Fumed Silica | Suspending Agent | 7 |
| HEMA | Monomer | 6 |
| Hydroxycyclohexyl Phenyl Ketone | Photoinitiator | 2.5 |
| Benzoyl Isopropanol | Photoinitiator | 2.5 |
| Ethyl Trimethylbenzoylphenylphosphinate | Photoinitiator | 1 |
| Red 30 | Colorant | 0.3 |
| Glitter | Additive | 2.5 |
| Parsol 1789 | UVA Filter | 6 |

Example 7

| Chemical Name | Function | Weight Percent (%) |
| --- | --- | --- |
| Urethane Acrylate/Methacrylate Oligomers | Curable Resin | 43.5 |
| Triethylene Glycol Dimethacrylate | Monomer/Crosslinker | 28 |
| Isobornyl Acrylate | Monomer | 9 |
| HEMA | Monomer | 3 |
| Parsol ® MCX | UVA Filter | 7.5 |
| Hydroxycyclohexyl Phenyl Ketone | Photoinitiator | 4 |
| Trimethylbenzoyl Diphenylphosphine Oxide | Photoinitiator | 1 |
| Isobornyl Methacrylate | Monomer | 1 |
| Glitters | Additives | 3 |

Example 8

| Chemical Name | Function | Weight Percent (%) |
|---|---|---|
| Urethane Acrylate/Methacrylate Oligomers | Curable Resin | 52 |
| HEMA | Monomer | 13 |
| Isobornyl Acrylate | Monomer | 10 |
| Hydroxycyclohexyl Phenyl Ketone | Photoinitiator | 2 |
| Benzoyl Isopropanol | Photoinitiator | 2 |
| Ethyl Trimethylbenzoylphenylphosphinate | Photoinitiator | 1 |
| Dimethicone | Plasticizer | 1 |
| Isobornyl Methacrylate | Monomer | 4 |
| Glitters | Additives | 5 |
| Parsol ® MCX | UVA Filter | 8 |
| Uvitex ® OB | UVB Filter | 2 |

Example 9

| Chemical Name | Function | Weight Percent (%) |
|---|---|---|
| Urethane Acrylate/Methacrylate Oligomers | Curable Resin | 49 |
| Triethylene Glycol Dimethacrylate | Monomer/Crosslinker | 27 |
| Parsol ® MCX | UVA Filter | 7 |
| HEMA | Monomer | 5 |
| Benzoyl Isopropanol | Photoinitiator | 2 |
| Hydroxycyclohexyl Phenyl Ketone | Photoinitiator | 2 |
| Ethyl Trimethylbenzoylphenylphosphinate | Photoinitiator | 1.5 |
| Titanium Dioxide | Pigment | 1 |
| Iron Oxide | Pigment | 1 |
| Red 21 | Pigment | 1 |
| Glitters | Additive | 3.5 |

Example 10

| Chemical Name | Function | Weight Percent (%) |
|---|---|---|
| Urethane Acrylate/Methacrylate Oligomers | Curable Resin | 59 |
| Hydroxypropyl Methacrylate | Monomer | 16.5 |
| HEMA | Monomer | 15 |
| Hydroxycyclohexyl Phenyl Ketone | Photoinitiator | 4.5 |
| Trimethylbenzoyl Diphenylphosphine Oxide | Photinitiator | 1.5 |
| Parsol ® MCX | UVA Filter | 3 |
| Glitters | Additive | 0.5 |

A composition suitable for forming a coating on a nail including any of the foregoing formulations may be formed according to any suitable technique. Representatively, in one embodiment, a curable resin(s), a monomer(s), a photoinitiator(s), chemical filter(s), a thixotrope(s), a solvent(s), a plasticizer(s), a suspending agent(s), an additive(s), a pigment(s), and colorant(s) may all be mixed together in one step to form the composition. Alternatively, the composition may be formed by mixing any one or more of the ingredients of any of the above-referenced exemplary formulations together in any order and in any combination.

In the foregoing specification, the invention has been described with reference to specific embodiments thereof. It will, however, be evident that various modifications and changes can be made thereto without departing from the broader spirit and scope of the invention as set forth in the appended claims. For example, although a nail coating such as a gel coating is disclosed herein, it is contemplated that the composition may form any type of curable covering for a nail, for example, an artificial nail, a top-coat which is applied over a nail lacquer, or the like. The specification is, accordingly, to be regarded in an illustrative rather than a restrictive sense.

What is claimed is:

1. A composition for forming a coating on a nail comprising:
    a curable resin;
    a monomer;
    a photoinitiator;
    a chemical filter in an effective amount sufficient to absorb ultraviolet (UV) light radiation and reduce exotherm;
    a thixotrope in an amount of at least 5 percent by weight of the total composition;
    and a solvent in an amount of at least 2 percent by weight of the total composition.

2. The composition of claim 1 wherein the chemical filter is capable of absorbing UV radiation within a wavelength range of UV radiation capable of exciting the photoinitiator.

3. The composition of claim 1 wherein the chemical filter is capable of absorbing ultraviolet A (UVA) radiation or ultraviolet B (UVB) radiation.

4. The composition of claim 1 wherein the chemical filter is selected from the group consisting of 2-ethylhexyl-3-(4-methoxyphenyl)-2-propenoate, 3-(4-methyl)benzylidene-bornan-2-one, 1-(4-tertbutylphenyl)-3-(4-methoxyphenyl)-propane-1, 3 dione, 2-cyano-3,3-diphenyl acrylic 2-ethylhexyl ester and 2,2'-(2,5-thiophenediyl)bis(5-tert-butylbenzoxazole).

5. The composition of claim 1 wherein the chemical filter is in an amount of from 1 percent to 15 percent by weight of the total composition.

6. The composition of claim 1 wherein the additive is a glitter or a pigment.

7. The composition of claim 1 wherein the photoinitiator is selected from the group consisting of benzoyl isopropanol, trimethylbenzoyl diphosphine oxide, trimethylbenzoyl diphenylphosphine oxide, hydroxycyclohexyl phenyl ketone, and ethyl trimethylbenzoylphenylphosphinate.

8. The composition of claim 1 wherein the photoinitiator is in an amount of from 1 percent to 10 percent by weight of the total composition.

9. The composition of claim 1 wherein the curable resin comprises a urethane (meth)acrylate oligomer.

10. The composition of claim 1 wherein the curable resin is in an amount of from 30 percent to 65 percent by weight of the total composition.

11. The composition of claim 1 wherein the monomer is selected from the group consisting of triethylene glycol dimethacrylate, hydroxypropyl methacrylate, isobornyl methacrylate, isobornyl acrylate, hydroxyethyl methacrylate (HEMA), hema maleate, PEG-4 dimethacrylate and ethyl methacrylate.

12. The composition of claim 1 wherein the monomer is in an amount of from 20 percent to 55 percent by weight of the total composition.

13. The composition of claim 1 wherein exotherm is reduced by at least 90 percent.

14. A photoreactive composition for forming a coating on a nail comprising:
    a curable resin in an amount of from 30 percent to 65 percent by weight of the composition;

a monomer in an amount of from 20 percent to 55 percent by weight of the total composition;

a photoinitiator in an amount of from 1 percent to 10 percent by weight of the total composition;

a chemical filter capable of absorbing ultraviolet (UV) light and reducing exotherm, wherein the chemical filter is in an amount of from 1 percent to 15 percent by weight of the total composition;

a thixotrope in an amount of at least 5 percent by weight of the total composition;

and a solvent in an amount of at least 2 percent by weight of the total composition.

15. The photoreactive composition of claim 14 further comprising:

an additive selected from one of a glitter or a pigment.

16. The photoreactive composition of claim 14 wherein the curable resin comprises a urethane (meth)acrylate oligomer.

17. The photoreactive composition of claim 14 wherein the chemical filter is selected from the group consisting of 2-ethylhexyl-3-(4-methoxyphenyl)-2-propenoate, 3-(4-methyl)benzylidene-bornan-2-one, 1-(4-tertbutylphenyl)-3-(4-methoxyphenyl)-propane-1, 3 dione, 2-cyano-3,3-diphenyl acrylic 2-ethyl-hexyl ester and 2,2'-(2,5-thiophenediyl)bis(5-tert-butylbenzoxazole).

18. The photoreactive composition of claim 14 further comprising:

a plasticizer in an amount of at least 2 percent by weight of the total composition.

19. A composition for forming a coating on a nail comprising:

a curable resin;

a monomer;

a photoinitiator, wherein the photoinitiator is excited by radiation within a first radiation wavelength range;

a chemical filter, wherein the chemical filter is capable of absorbing radiation within the first radiation wavelength range and reducing exotherm;

a thixotrope in an amount of at least 5 percent by weight of the total composition; a solvent in an amount of at least 2 percent by weight of the total composition; and an additive.

20. The composition of claim 19 wherein the first radiation wavelength range is within one of a 365 nm region or a 405 nm region.

21. The composition of claim 19 wherein the photoinitiator is a first photoinitiator, the composition further comprising a second photoinitiator, wherein the second photoinitiator is excited within a second radiation wavelength range different from the first radiation wavelength range.

22. The composition of claim 21 wherein the chemical filter is capable of absorbing radiation in the first wavelength range or the second wavelength range.

* * * * *

UNITED STATES PATENT AND TRADEMARK OFFICE
CERTIFICATE OF CORRECTION

| | | |
|---|---|---|
| PATENT NO. | : 9,044,405 B2 | Page 1 of 1 |
| APPLICATION NO. | : 13/778765 | |
| DATED | : June 2, 2015 | |
| INVENTOR(S) | : Sunil J. Sirdesai | |

It is certified that error appears in the above-identified patent and that said Letters Patent is hereby corrected as shown below:

In the Claims

Column 10, Claim 19, lines 13-15, delete "the total composition; a solvent in an amount of at least 2 percent by weight of the total composition; and an additive." and insert
-- the total composition;
   a solvent in an amount of at least 2 percent by weight of the total composition;
   and an additive. --

Signed and Sealed this
Twenty-third Day of February, 2016

Michelle K. Lee
*Director of the United States Patent and Trademark Office*